United States Patent [19]

Panneman et al.

[11] 4,028,380
[45] June 7, 1977

[54] HYDRAZINO-IMIDAZOLE DERIVATIVES

[75] Inventors: Harm Jan Panneman; Antonius Hermanus Nicolaas Maria Bruins, both of Oss, Netherlands

[73] Assignee: Akzona Incorporated, Asheville, N.C.

[22] Filed: Dec. 10, 1975

[21] Appl. No.: 639,495

Related U.S. Application Data

[62] Division of Ser. No. 579,633, May 21, 1975.

[30] Foreign Application Priority Data

June 1, 1974 Netherlands .................. 74.07469

[52] U.S. Cl. .................. 260/309.6; 260/247.5 R; 260/256.4 H; 260/256.4 N; 260/256.5 R; 260/293.62; 260/309; 260/309.7; 260/313.1; 260/326.5 L; 260/326.86; 260/564 F; 260/564 A; 424/248.56; 424/251

[51] Int. Cl.² .................. C07D 233/50

[58] Field of Search ............ 260/309.6, 309.7, 309, 260/256.4 H, 256.4 N, 256.5 R

[56] References Cited

UNITED STATES PATENTS

| | | | |
|---|---|---|---|
| 3,480,630 | 11/1969 | Stahle et al. | 260/309.6 |
| 3,528,968 | 9/1970 | Houlihan et al. | 260/309.6 |
| 3,530,140 | 9/1970 | Kummer et al. | 260/309.6 |
| 3,632,602 | 1/1972 | Wilhelm | 260/309.6 |

Primary Examiner—Natalie Trousof
Attorney, Agent, or Firm—Francis W. Young; Hugo E. Weisberger

[57] ABSTRACT

The invention relates to novel amidino-hydrazone derivatives of the general formula:

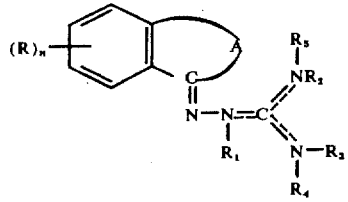

in which the dotted lines mean one extra bond starting from the (guanidine-)carbon atom to one of the adjacent nitrogen atoms, and A stands for methylene, ethylene, propylene or butylene, which groups may optionally be substituted with alkyl (1–4 C), R stands for hydroxy, alkyl (1–4 C), alkylthio or alkoxy (1–4 C), halogen, trifluoromethyl, nitro, amino, hydroxymethyl, acyloxy or an alkylenedioxy group, $n$ is the number 0, 1, 2, 3 or 4, $R_1$, $R_4$ and $R_5$ represent hydrogen or alkyl (1–4 C), with the proviso that one of them is absent in view of the presence of the double bond, $R_2$ and $R_3$ stand for hydrogen, alkyl (1–4 C), aralkyl, aryl, hydroxy or amino, with the proviso that $R_2 + R_3$ together may also represent a saturated or unsaturated alkylene group with 2 or 3 carbon atoms, or $R_3 + R_4$ together with the nitrogen atom may also stand for a heterocyclic five- or six-membered ring, as well as the pharmaceutically acceptable acid addition salts thereof, having valuable, antihypertensive and antithrombosis activities.

6 Claims, No Drawings

HYDRAZINO-IMIDAZOLE DERIVATIVES

CROSS-REFERENCE TO RELATED APPLICATION

This application is a division of application Ser. No. 579,633, filed on May 21, 1975.

The invention relates to novel amidino-hydrazone derivatives, to processes for the preparation of these compounds and to pharmaceutical preparations containing these novel amidino-hydrazone derivatives as the active component.

It has been found that amidino-hydrazone derivatives of the general formula:

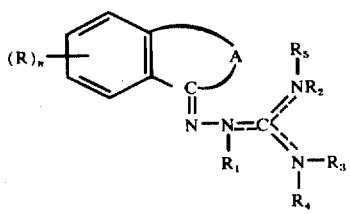

I in which the dotted lines mean one extra bond starting from the (guanidine-)carbon atom to one of the adjacent nitrogen atoms, and A stands for methylene, ethylene, propylene or butylene, which groups may optionally be substituted with alkyl (1–4 C), R stands for hydroxy, alkyl (1–4 C), alkylthio or alkoxy (1–4 C), halogen, trifluoromethyl, nitro, amino, hydroxymethyl, acyloxy or an alkylenedioxy group, $n$ is the number 0, 1, 2, 3 or 4, $R_1$, $R_4$ and $R_5$ represent hydrogen or alkyl (1–4 C), with the proviso that one of them is absent in view of the presence of the double bond, $R_2$ and $R_3$ stand for hydrogen, alkyl (1–4 C), aralkyl, aryl, hydroxy or amino, with the proviso that $R_2 + R_3$ together may also represent a saturated or unsaturated alkylene group with 2 or 3 carbon atoms, or $R_3 + R_4$ together with the nitrogen atom may also stand for a heterocyclic five- or six-membered ring, as well as the pharmaceutically acceptable acid addition salts thereof, are very valuable biologically active substances.

The compounds I have a very strong antihypertensive activity, especially in case of oral administration, which property can be applied for the normalization of undesirably high blood pressures in renal, neurogenic or essential hypertension. Moreover the compounds I have biocide and anti-thrombosis activities, more in particular they inhibit the aggregation of blood platelets and accelerate the disaggregation of aggregates of blood platelets already formed.

The compounds according to the general formula I can be synthesised in a manner usual for analogous compounds.

The most simple, direct and generally applicable way for the preparation of the compounds I, is the direct condensation of an amidino-hydrazine derivative of the general formula II:

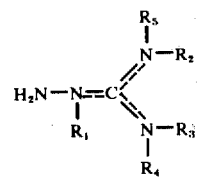

II or an acid addition salt thereof, in which the dotted lines, $R_1$, $R_2$, $R_3$, $R_4$ and $R_5$ have the meanings mentioned before, with an oxo-containing compound of the general formula:

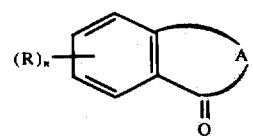

III in which R, A and $n$ have the meanings mentioned before.

The starting products III are well-known compounds to which belong for example: 1-benzocyclobutenone, 1-indanone and α-tetralone.

The reaction conditions for this condensation reaction are the usual conditions for the preparation of hydrazones.

An indirect manner for the preparation of the compounds I is a synthesis in which the last step is a reaction of a compound with the general formula IV:

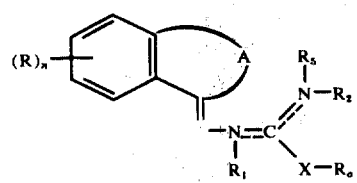

IV or an acid addition salt thereof, in which the dotted lines, R, $R_1$, $R_2$, $R_5$, A and $n$ have the meanings mentioned before, X is oxygen or sulphur and $R_0$ a lower alkyl group preferably a methyl group, with an amine of the formula V:

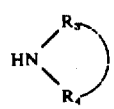

V or an acid addition salt thereof, in which $R_3$ and $R_4$ have the aforesaid meanings with the proviso that $R_3$ may additionally stands for an aminoalkyl/-or aminoalkenyl group with 2 or 3 carbon atoms, if $R_2$ in formula IV stands for hydrogen.

This reaction is carried out under the usual conditions for the preparation of guanidines. If a diamine of formula V ($R_3$ is aminoalkyl or aminoalkenyl) is used, a ringclosure is effected additionally besides the aforesaid substitution of the $XR_0$ moiety (in formula IV).

The latter ring closure is preferably performed at an elevated temperature; in that case the ammonia formed during the reaction can be removed more readily.

Amines according to the general formula V that can be used in the above-mentioned synthesis are, for example: ammonia, methylamine, dimethylamine, diethylamine, isopropylamine, dibutylamine, pyrrole, pyrrolidine, pyrroline, piperidine, imidazole, morpholine, 1,2-diamino-ethane, 1-amino-2-methylamino-ethane, hydrazine, hydroxylamine, etc.

The starting products IV are prepared in a conventional manner, for instance by reacting the oxo compound III with an iso(thio)urea derivative of the formula:

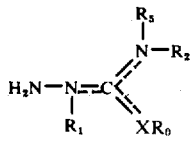

in which the dotted lines, $R_1$, $R_2$, $R_5$, X and $R_0$ have the aforesaid meanings.

Another method for the preparation of the compounds I is starting from a compound of the general formula VI:

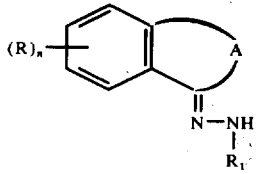

in which R, $R_1$, A and $n$ have the meanings mentioned before.

This starting product VI can be prepared for example by reacting a compound of formula III with hydrazine or an alkylhydrazine.

In various manners the starting product VI may be converted into the final product according to formula I, for instance by a. reacting VI with a cyanamide or carbodi-imide of the formula VII:

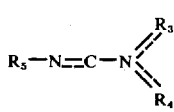

in which the dotted lines, $R_3$, $R_4$ and $R_5$ have the aforesaid meanings, in a conventional manner for the preparation of guanidino-derivatives, or b. reacting VI with an iso-urea or isothio-urea derivative of the formula VIII:

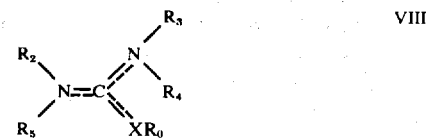

in which the dotted lines, $R_2$, $R_3$, $R_4$, $R_5$, X and $R_0$ have the aforesaid meanings, in a conventional manner for the preparation of guanidino-derivatives.

The compounds of formula I are of alkaline nature; they can therefore, depending on the medium in which they are prepared, be obtained as free base or as acid addition salt. The free base can also be prepared from the salt in the usual way, for example by reacting with a strong base or with the aid of an ion-exchanger.

A pharmaceutically acceptable acid addition salt is obtained by reacting the free base I with a suitable inorganic or organic acid, such as hydrochloric acid, hydrobromic acid, hydroiodic acid, phosphoric acid, acetic acid, propionic acid, glycollic acid, maleic acid, fumaric acid, malonic acid, succinic acid, tartaric acid, lactic acid, citric acid, ascorbic acid, salicylic acid, benzoic acid, etc.

Some compounds according to the invention have an asymmetric carbon, namely those compounds I, wherein A stands for an alkylene (1-4 C) group which is substituted with a lower alkyl group. Besides the racemic mixture also separate optical enantiomers can be obtained in that case.

These optically active final products I, which also belong to the compounds according to the invention may be prepared in a conventional manner by resolution of the racemic final product. It is preferable, however, to start the synthesis in that case from an optically active starting product, for example an optically active compound according to formula III.

By an alkyl group used in the various definitions accompanying the general formula I is meant a branched or linear alkyl group of 1-4 carbon atoms, such as methyl, ethyl, propyl, isopropyl, butyl and tert. butyl. The alkyl group in the alkylthio and alkoxy moieties used in the definition of R has the same meaning.

By an aryl group mentioned in the definition of $R_2$ or $R_3$ is preferably meant a substituted or non-substituted phenyl group, such as phenyl, p-chlorophenyl, p-bromophenyl, 2,6-dichlorophenyl, p-methoxyphenyl, p-tolyl, o,p-dimethylphenyl, etc.

By an aralkyl group mentioned in the definition of $R_2$ or $R_3$ is preferably meant a substituted (particularly a phenyl or halogen substituted) or non-substituted phenylalkyl group, in which the alkyl group is an aliphatic hydrocarbon with 1-6 carbon atoms, such as benzyl, phenylethyl, diphenylmethyl, p-chlorophenylethyl, phenylpropyl, phenylpropen-2-yl, phenylbutyl, etc. or a phenyl moiety fused to a cyclo-aliphatic hydrocarbon with 5 to 8 carbon atoms, such as indanyl or 2,2-dimethylindanyl.

By an acyloxy group mentioned in the definition of R is meant a group derived from a lower aliphatic carboxylic acid with 1–4 carbon atoms, such as acetic acid, propionic acid, butyric acid. Preferably the acetoxy group is employed.

If $n \geq 2$ the substituents (R) at the benzo ring may be the same or different groups.

The compounds according to the invention can be administered orally, locally and parenterally, preferably in a daily dosage of between 0.0001 and 50 mg per kg body weight.

Being mixed with suitable carriers the compounds I can be compressed into solid dosage units, such as pills, tablets or coated tablets; they can also be processed into capsules. By means of suitable diluents the compounds I can be processed into injection preparations in the form of solutions, suspensions or emulsions.

A pharmaceutical preparation for oral administration is to be preferred.

Very suitable compounds I that can be used in antihypertensive preparations are the compounds of formula I in which the benzo ring is unsubstituted, particularly those of the indane- and benzocyclobutene-series, and the 4- or 6-monosubstituted or 4,6-disubstituted compounds I belonging to the benzocyclobutene series.

Very suitable compounds I that can be used for preventing or combatting thrombosis are the 4- or 7-monosubstituted- or 4,7-disubstituted compounds I belonging to the indane-series and the 4- and 6-monosubstituted or 4,6-disubstituted compounds I, belonging to the benzocyclobutene series, and more in particular those compounds I whereby $R_2$ and $R_3$ together represent a saturated or an unsaturated alkylene group, particularly an ethylene group.

EXAMPLE I 4,6-dimethylbenzocyclobutenone-1-amidohydrazone.HCl and .CH₃COOH

To 2.92 g of 4,6-dimethylbenzocyclobutenone-1 (J. Org. Chem. 31, 2244 (1966)) dissolved in 25 ml of glacial acetic acid, 2.25 g of aminoguanidine.HCl are added, whereafter the mixture is stirred for 4 hours at room temperature. Then 25 ml of ether are added, and the precipitate formed is filtered off and recrystallised from water.

Yield: 4.0 g; melting point: 256°–258° C.

If the reagent aminoguanidine.bicarbonate is used instead of aminoguanidine.HCl, the acetate instead of hydrochloric acid salt is obtained. Melting point of the acetate: 213°–214° C.

EXAMPLE II 4,7-dimethylindanone-1-amidinohydrazone.HCl

To 4.0 g of 4,7-dimethylindanone-1 (J.A.C.S. 72, 3286 (1950)), dissolved in 30 ml of glacial acetic acid, 2.8 g of amidinoguanidine.HCl are added, whereafter the mixture is stirred for 48 hours at room temperature. Then 30 ml of ether are added after which the precipitate formed is filtered off and recrystallised from ethanol.

Yield: 5.0 g; melting point: 234°–235° C.

EXAMPLE III 1-(4,6-dimethylbenzocyclobutenylidene-amino)-2-methylguanidine.HCl To 2.92 g of 4,6-dimethylbenzocyclobutenone-1, dissolved in 25 ml of glacial acetic acid, 2.49 g of 1-methyl2-aminoguanidine.HCl are added. After stirring for 4 hours at room temperature, 25 ml of ether are added. The precipitate formed is filtered off and recrystallised from ethanol/acetic acid/ether.

Yield: 4.2 g; melting point: 226°–227° C.

EXAMPLE IV 4-chloro-7-methyl-indanone-1-amidinohydrazone.HCl

To 2.3 g of 4-chloro-7-methylindanone-1 (J. Org. Chem. 14, 480, (1949)) dissolved in 125 ml of glacial acetic acid, 1.4 g of aminoguanidine.HCl is added. After stirring the mixture for 48 hours at room temperature 15 ml of ether are added after which the precipitate formed is filtered off and recrystallized from ethanol.

Yield: 1.7 g; melting point: 267°–268° C.

EXAMPLE V 2-(1-indanylidene-hydrazino)-imidazoline.HCl

To 5.3 g of indanone-1, dissolved in 40 ml of glacial acetic acid, 5.5 g of 2-hydrazino-2-imidazoline.HCl are added. After stirring the mixture for 16 hours at room temperature, the precipitate is filtered off and recrystallised from ethanol-ether.

Yield: 8.2 g; melting point; 261°–263° C.

In a corresponding manner the compounds 2-(1-indanylidene-hydrazino)-imidazol.hydrochloride and 2-(1-indanylidene-hydrazino)-pyrimidine.hydrochloride are prepared by condensation of indanone-1 with 2-hydrazino-imidazol and 2-hydrazino-pyrimidine respectively.

EXAMPLE VI 4-methyl-7-chloro-indanone-1-amidinohydrazone.HCl

To 2.7 g of 4-methyl-7-chloro-indanone-1 (J. Org. Chem. 14, 480, (1949)) dissolved in 15 ml of glacial acetic acid, 1.5 g of aminoguanidine.HCl is added. After stirring the mixture for 16 hours at room temperature, the precipitate is filtered off and recrystallised from 90% ethanol.

Yield: 1.5 g; melting point: >250° C.

In the same manner are prepared:
4-methyl-indanone-1-amidinohydrazone.HCl; melting point >300° C.
4-methyl-7-acetoxy-1-amidinohydrazone.HCl; melting point 233° C (dec.),
4-chloro-indanone-1-amidinohydrazone.HCl; melting point 292°–295° C (dec.),
7-methyl-indanone-1-amidinohydrazone.HCl; melting point 274° C (dec.),
5-methyl-indanone-1-amidinohydrazone.HCl; melting point >275° C,
6-methyl-indanone-1-amidinohydrazone.HCl; melting point >250° C,
4-methyl-7-hydroxy-indanone-1-aminodinohydrazone.CH₃COOH; melting point 225°–227° C (dec.),
4,7-di-isopropyl-indanone-1-amidinohydrazone.HCl; melting point 274°–277° C (dec.), 4-methyl-7-amino-indanone-1-amidinohydrazone.2 HCl; melting point >250° C.

EXAMPLE VII

2-[1-(3-methyl-indanylidene-hydrazino)]-imidazoline.HCl

To 5.8 g of 3-methyl-indanone-1 (J.A.C.S. 62, 3499 (1940)), dissolved in 40 ml of glacial acetic acid, 5.5 g of 2-hydrazino-2-imidazoline.HCl are added. After being stirred for 16 hours at room temperature, the reaction mixture is evaporated and the residue recrystallised from ethanol-ether.

Yield: 8.5 g; melting point: 255°–260° C.

EXAMPLE VIII 4,5,6,7-tetramethylindanone-1-amidinohydrazone (acetate and hydrochloride To 3.3 g of 4,5,6,7-tetramethylindanone-1 (Ber. 97, 3461 (1964)), dissolved in 17 ml of glacial acetic acid, 1.9 g of aminoguanidine.HCl is added. After stirring the mixture for 72 hours at room temperature, the precipitate is filtered off.

Yield: 4.4 g; melting point: 265°–270° C (HCl salt).

This HCl salt is converted into the free base and then reacted with acetic acid to obtain the acetate. Recrystallisation from methanol yields 1.8 g acetate salt, melting point 224°–225° C.

EXAMPLE IX 1-(1-indanylidene-amino)-2,3-dimethylquanidine.HCl

To 5.3 g of indanone-1, dissolved in 40 ml of glacial acetic acid, 5.5 g of 2-amino-1,3-dimethyl-guanidine.HCl are added. After stirring the mixture for 16 hours at room temperature the precipitate is filtered off and recrystallised from ethanol.

Yield: 9.5 g; melting point: 259°–261° C.

In the same manner is prepared: 1-[1-(4,7-dimethylindanylidene-amino)]-2,3-dimethylguanidine.HCl, melting point: 233°–235° C.

EXAMPLE X

2-[1-(4,6-dimethylbenzocyclobutenylidene-hydrazino)]-imidazoline.HCl

To 4.7 g of 4.6-dimethylbenzocyclobutenone-1, dissolved in 40 ml of glacial acetic acid, 4.4 g of 2-hydrazinoimidazoline.HCl are added. After stirring the mixture for 4 hours at room temperature, 40 ml of ether are added after which the precipitate formed is filtered off and recrystallised from ethanol-ether.

Yield: 6.6 g; melting point: 265°–268° C. The compound contains 1 mol $H_2O$.

EXAMPLE XI 1-(4,6-dimethylbenzocyclobutenylidene-amino)-2-hydroxyguanidine.HBr To 0.67 g of 4,6-dimethylbenzocyclobutenone-1, dissolved in 10 ml of glacial acetic acid, 0.8 g of 1-amino-2-hydroxyguanidine.HBr is added. After stirring the reaction mixture for 16 hours at room temperature, 10 ml of ether area added. The precipitate is filtered off and recrystallised from ethanol-ether.

Yield: 0.7 g; melting point: 196°–197° C.

EXAMPLE XII 1-(1-indanylidene-amino)-2-methylguanidine.HCl

A. Direct route 0.66 g of 1-indanone, dissolved in 5 ml of glacial acetic acid, is added to 0.68 g of 1-methyl-2-aminoguanidine.HCl, whereafter the mixture is stirred for 20 hours at room temperature. Then 5 ml of ether are

EXAMPLE XIII a.
4,6-dimethylbenzocyclobutenone-1-thiosemicarbazone

To 1.46 g of 4,6-dimethylbenzocyclobutenone-1, dissolved in 25 ml of ethanol, 0.91 g of thiosemicarbazide is added. After refluxing for 3 hours the mixture is cooled down and the precipitate formed filtered off and dried.

Yield: 2.0 g; melting point: 230°–232° C.

b.
1-(4,6-dimethylbenzocyclobutenylidene-amino)-2-ethyl-isothiourea.HBr

To 8.0 g of 4,6-dimethylbenzocyclobutenone-1-thiosemicarbizone, suspended in 35 ml of ethanol, 3.24 ml of ethylbromide are added. After refluxing for 3 hours the mixture is cooled down and the precipitate formed filtered off and dried.

Yield: 6.2 g; melting point: 214°–216° C.

The same product is also prepared in the following manner. To 2.92 g of 4,6-dimethylbenzocyclobutenone-1, dissolved in 50 ml of ethanol 4.0 g of S-ethylisothiosemicarbazide.HBr are added. After refluxing for 3 hours the mixture is cooled down and the precipitate formed filtered off and dried.

Yield: 5.3 g; melting point: 212°–214° C.

c.
1-(4,6-dimethylbenzocyclobutenylidene-amino)-2-methylisothiourea.HJ

To 1.46 g of 4,6-dimethylbenzocyclobutenone-1, dissolved in 25 ml of ethanol, 2.33 g of S-methylisothiosemicarbazide.HJ are added, after which the mixture is refluxed for 3 hours and then cooled to ambient temperature. The added, after which the precipitate formed is filtered off and recrystallised from ethanol-ether.

Yield: 1.0 g; melting point: 265°–267° C.

B. Indirect route 1. 1-(1-indanylidene-amino)2-methylisothiourea.HJ

To 5.28 g of 1-indanone, dissolved in 100 ml of ethanol, 9.32 g of S-methylisothiosemicarbazide.HJ are added. After refluxing for 3 hours the mixture is cooled down and the precipitate is filtered off and dried.

Melting point: 222°–223° C; yield: 10.4 g.

2. 1-(1-indanylidene-amino)-2-methylguanidine.HCl 1.73 g of 1-indanylidene-amino-2-methylisothiourea. HJ, obtained in B.1. is dissolved in 3.2 ml of dimethylsulfoxide, whereafter 3.2 ml of 3.1 N methylamine solution in ethanol are added. The mixture is stirred for 72 hours at room temperature and further for 16 hours at 40° C. Then the reaction mixture is evaporated to dryness and the residue recrystallised from ethanol-ether.

Melting point of the HJ salt: 233°–235° C; yield: 1.3 g. This HJ salt is converted into the HCl salt (via the free base). Melting point: 264°–267° C; yield: 0.7 g.

Yield: 6.2 g; melting point: 214°–216° C. The same product is also prepared in the following manner. To 2.92 g of 4,6-dimethylbenzocyclobutenone-1, dissolved in 50 ml of ethanol 4.0 g of S-ethylisothiosemicarbazide.HBr are added. After refluxing for 3 hours the mixture is cooled down and the precipitate formed filtered off and dried. precipitate formed is filtered off and recrystallised from ethanol. Melting point: 209°–210° C; yield: 1.9 g.

d. By reacting the compound obtained in (b) or (c) with various amines in the manner described in example XII B.2., the following compounds are obtained:
1. by a reaction of "b" with ammonia and converting the compound obtained into the HCl salt: 4,6-dimethylbenzocyclobutenone-1-amidinohydrazone.HCl.
2. by a reaction of "c" with dimethylamine and conversion into the HCl salt: 1-(4,6-dimethylbenzocyclobutenylidene-amino)-2,2-dimethylguanidine.HCl.
3. by reaction of "c" with methylamine and conversion into the HCl salt: 1-(4,6-dimethylbenzocyclobutenylidene-amino)-2-methylguanidine.HCl.
4. by reaction of "b" with hydroxylamine: 1-(4,6-dimethylbenzocyclobutenylidene-amino)-2-hydroxyguanidine.HBr.
5. by reaction of "b" with hydrazine: 1-(4,6-dimethylbenzocyclobutenylidene-amino)-2-aminoguanidine.HBr.
6. by reaction of "b" with morpholine: 1-(4,6-methylbenzocyclobutenylidene-amino)-2-(anhydrobis-βhydroxyethyl)guanidine.HBr.

EXAMPLE XIV 1-(4,6-dimethylbenzocyclobutenylidene-amino)-2-aminoguanidine.HBr To 1.46 g of 4,6-dimethylbenzocyclobutenone-1, dissolved in 12.5 ml of glacial acetic acid, 1.7 g of 1,2-diaminoguanidine.HBr is added. After stirring for 48 hours at room temperature, the precipitate formed is filtered off and dried. Yield: 2.5 g; melting point: 236°–241° C.

EXAMPLE XV 3,4,5,6-tetramethyl-benzocyclobutenone-1-amidinohydrazone. $CH_3COOH$ To 5.22 g of 3,4,5,6-tetramethyl-benzocyclobutenone-1 (J.O.C. 31, 2244 (1966)), dissolved in 35 ml of glacial acetic acid, 4.08 g of aminoguanidine.$H_2CO_3$ are added. After stirring for 24 hours at room temperature 70 ml of ether are added after which the precipitate formed is filtered off and recrystallised from methanol. Melting point: 222°–223° C; yield: 5.0 g.

EXAMPLE XVI 6-amino-indanone-1-amidinohydrazone.2 HCl 3.67 g of 6-amino-indanone-hydrochloride (J. Chem. Soc. 123, 1469 (1923)) are suspended in 35 ml of glacial acetic acid, whereafter 2.21 g of aminoguanidine.HCl are added. The mixture is stirred for 24 hours at room temperature after which 35 ml of ether are added. The precipitate formed is filtered off, resuspended in 50 ml of ethanol and stirred again.

Then the precipitate is filtered off and dried. Yield: 4.5 g; melting point: >280° C.

EXAMPLE XVII 6-nitro-indanone-1-amidinohydrazone.$CH_3COOH$

To 5.31 g of 6-nitro-indanone (Chem. Ber. 102, 3656 (1969)), dissolved in 40 ml of glacial acetic acid, 4.08 g of aminoguanidine.$H_2CO_3$ are added. After stirring for 24 hours at room temperature, the precipitate formed is filtered off and recrystallised from glacial acetic acid. Melting point: 215–217° C (decomp.); yield: 7.25 g.

EXAMPLE XVIII

Indanone-1-amidinohydrazone.$HNO_3$ 28.0 g of 1-indanone (J.A.C.S. 88, 2233, 1966) and 58.1 g of aminoguanidine.$HNO_3$ are stirred for 20 hours at room temperature in 250 ml of glacial acetic acid and then poured out into 500 ml of water. The crystals formed are filtered off and washed again with water. After drying over $P_2O_5$ in vacuo, 36 g of indanone-1-amidinohydrazone. nitrate are obtained. Melting point: 275°–276° C.

EXAMPLE XIX 2-methylindanone-1-amidinohydrazone.$HNO_3$ (racemate)

6.5 g of racemic 2-methylindanone-1(Bull. Soc. Chim. France 1952, 462) and 12.2 g of aminoguanidine.$HNO_3$ are stirred for 20 hours at room temperature in 175 ml of glacial acetic acid and then poured out into 150 ml of water. The crystals formed are filtered off, washed again with water and dried in vacuo over $P_2O_5$. Melting point: 232°–234° C; yield: 7.0 g.

EXAMPLE XX 3-methylindanone-1-amidinohydrazone.$HNO_3$ (racemate)

6.6 g of reacemic 3-methylindanone-1 (J. Am. Chem. Soc. 62, 3499 (1940)) added 13.7 g of aminoguanidine.$HCO_3$ are stirred in 20 ml of glacial acetic acid for 20 hours at room temperature and then poured out into 250 ml of water. The crystals are filtered off, washed again with water and dried in vacuo. Melting point: 265° C; yield: 14 g.

EXAMPLE XXI (α-tetralone)-amidinohydrazone.HCl 7.3 g of α-tetralone (Org. Synth. 35, 95 (1955)) and 5.5 g of aminoguanidine.HCl are stirred in 50 ml of glacial acetic acid for 18 hours at room temperature. Then the mixture is evaporated to dryness and the resulting oil crystallised in ethanol-ether.

Melting point: 167°–169° C; yield: 9.5 g.

EXAMPLE XXII 3,3-dimethylindanone-1-amidinohydrazone.HCl 8.15 g of 3,3-dimethylindanone-1 (Bull. Soc. Chim. France 1947, 812) and 5.6 g of aminoguanidine.HCl are stirred for 18 hours in 50 ml of glacial acetic acid at room temperature. Then the mixture is evaporated and crystallised in ethanol-ether. Melting point: 195°–197° C; yield: 9.3 g.

EXAMPLE XXIII 5,6-dimethoxyindanone-1-amidinohydrazone.HCl 2.5 g of 5,6-dimethoxyindanone-1 (Ber. 102, 3656 (1969)) and 1.4 g of aminoguanidine.HCl are stirred for 18 hours in 30 ml of glacial acetic acid at room temperature. Then the mixture is diluted with 30 ml of ether and the crystals formed sucked off and dried. Melting point: 198°–200° C; yield: 3.6 g.

In the same manner is prepared: 5,6-methylenedioxyindanone-1-amidinohydrazone.HCl and 5,6-di(methylmercapto) indanone-1-amidinohydrazone.HCl.

EXAMPLE XXIV

In a similar way as described for some 5,6-di-substituted-indanone-1-amidinohydrazones in example XXIII, the following 4,7-dis-substituted-indanone-1-amidinohydrazone derivatives are prepared:

4,7-dimethoxy-indanone-1-amidinohydrazone acetate, melting point 208° C (dec.), 1-(4,7-dimethyl-1-indanylidene-amino)-2-diphenylmethylguanidine.HCl; melting point 271°–273° C, 1-(4,7-dimethyl-1-indanylidene-amino)-2(2',6'-dichlorophenyl)-guanidine.HCl; melting point >275° C, 1-(4,7-dimethyl-1-indanylidene-amino)-2(2',2'-dimethyl-1'-indanyl)-3-methyl-guanidine.HBr; melting point 223° C (dec.).

EXAMPLE XXV (−)-S-3-methylindanone-1-amidinohydrazone.HCl 4.9 g of (+)-S-3-methylindanone-1 (Acta Chem. Scand. 18, 1483 (1964)) and 3.7 g of aminoguanidine.HCl in 40 ml of glacial acetic acid are stirred for 18 hours at room temperature. After evaporation to dryness the residue is recrystallised from ethanol-ether, yielding 4.35 g of (−)-S-3-methylindanone-1-amidinohydrazone.HCl, melting point: 194°–196° C; $[\alpha]^{20}_D = -67.3°$ (c = 1.3; $CH_3OH$).

EXAMPLE XXVI (+)-R-3-methylindanone-1-amidinohydrazone.HCl 1.5 g of (−)-R-3-methylindanone-1 (Acta Chem. Scand. 18, 1483 (1964)) and 1.14 g of aminoguanidine.HCl in 15 ml of glacial acetic acid are stirred for 18 hours at room temperature. After evaporation to dryness the residue is recrystallised from ethanol-ether, yielding 1.2 g of (+)-R-3-methylindanone-1-amidinohydrazone.HCl, melting point: 194°–196° C; $[\alpha]_D^{20} = +67.2°$ (c = 0.8; $CH_3OH$).

EXAMPLE XXVII

A. 1-(1-indanylidene-amino)-1-methyl-guanidine.HCl

To 3.1 g of indanone-1-methylhydrazone, dissolved in 20 ml of ethanol, 2.5 g of S-methyl-isothiourea hydrochloride are added. The reaction mixture is refluxed for 24 hours and then cooled down. Ether (40 ml) is added, after which the precipitate formed is filtered off and recrystallised from ethanol/ether.

Yield: 1.2 g; melting point: 215°–225° C.

B. Starting from 3,3-dimethylindanone-1-hydrazone is obtained in the same manner as described in A.: 3,3-dimethylidanone-1-amidinohydrazone.HCl. Melting point: 194°–197° C. Starting from 6-aminoindanone-1-hydrazone is obtained 6-amino-indanone-1-amidinohydrazone.HCl. Melting point: >280° C. Starting from indanone-1-hydrazone is obtained: indanone1-amidinohydrazone.HCl (Example XVIII).

C. The same compound as prepared in A. is also obtained by stirring a mixture of cyanamide and indanone-1-methylhydrazone.HCl in toluene for 24 hours at a temperature of about 70° C. Melting point: 215°–220° C.

EXAMPLE XXVIII 4-hydroxy-indanone-1-amidinohydrazone.HCl

A mixture of 110 mg of 4-hydroxy-indanone-1 and 148 mg of amino-guanidine.HCl is refluxed for 20 hours in absolute methanol and then cooled down. The precipitate formed is filtered off.

Yield: 179 mg; decomposition point above 270° C.

Rf in butanol:acetic acid:water (4:1:1) = 0.54 on $SiO_2$.

EXAMPLE XXIX

In the same manner as described in Example V the following compounds are prepared:

2-[1-(4,7-dimethylindanylidene-hydrazino)]-imidazoline.HCl, melting point >300° C 2-[1-(4,7-dimethoxyindanylidene-hydrazino)]-imidazoline. HCl, melting point 255° C (dec.)

2-[1-(4,7-dimethylindanylidene-methylhydrazino)]-imidazoline.HCl, melting point 181°–182° C 2-[1-(7-methylindanylidene-hydrazino)]-imidazoline.HCl, melting point >280° C 2-[1-(4-methyl-7-hydroxy-indanylidene-hydrazino)]-imidazoline.HCl, melting point 242°–244° C 2-[1-(4,7-dimethylindanylidene-methylhydrazino)]-N-methylimidazoline.HCl, melting point 210°–212° C 2-[1-(4,7-dimethylindanylindanylidene-hydrazino)]-N-methylimidazoline.HCl, melting point 270° C (dec.)

2-[1-(4-methyl-7-chloro-indanylidene-hydrazino)]-imidazoline.HCl, melting point >250° C (dec.)

2-[1-(4-methyl-7-acetoxy-indanylidene-hydrazino)]-imidazoline.HCl, melting point 204° C (dec.)

2-[1-(4-methylindanylidene-hydrazino)]-imidazoline.HCl, melting point >250° C.

2-[1-(4-chloro-indanylidene-hydrazino)]-imidazoline.HCl, melting point >250° C.

2-[1-(5,6-dimethoxy-indanylidene-hydrazino)]-imidazoline. HCl, melting point 265° C (dec.)

2-[1-(4,7-dimethylindanylidene-hydrazono)]-N,N'-dimethylimidazolidine.HCl (oil), Rf in butanol:acetic acid: water (4:1:1) = 0.50 on $SiO_2$.

If tautomerism is possible with regard to the position of the double bond of the guanidine moiety of the compounds of general formula I, this double bond might also be present in conjugated position with respect to the double bond attached to the benzocycloalkylene group. In that case an alternative nomenclature can be used; for example the first compound of Example XXIX may also be named: 2-[1-(4,7-dimethylindanylidene-hydrazono)]-imidazolidine.HCl.

We claim:

1. A compound of the formula:

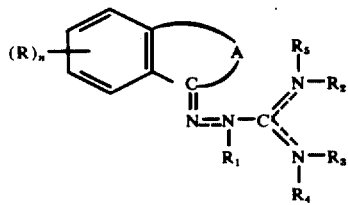

or a pharmaceutically acceptable acid addition salt thereof, in which the dotted lines mean one extra bond starting from the (guanidine-) carbon atom to one of the adjacent nitrogen atoms, and A represents methylene, ethylene, propylene or butylene, which groups may optionally be substituted with alkyl having 1 to 4 carbon atoms;

R represents hydroxy, alkyl having 1 to 4 carbon atoms, alkylthio or alkoxy having 1 to 4 carbon atoms, halogen, trifluoromethyl, nitro, amino, hydroxymethyl, lowr alkanoyloxy, or a methylenedioxy group, the latter insofar as n is the number 2 and two adjacent carbon atoms atoms of the benzo ring are involved;

n is the number 0, 1, 2, 3 or 4 with the proviso that where n is 3 or 4, R is only alkyl;

$R_1$, $R_4$ and $R_5$ represent hydrogen or alkyl having 1 to 4 carbon atoms, with the proviso tht one of them is absent in view of the presence of the double bond; and wherein $R_2$ together with $R_3$ represents an alkylene or alkenylene group with 2 carbon atoms.

2. A compound according to claim 1 of the formula:

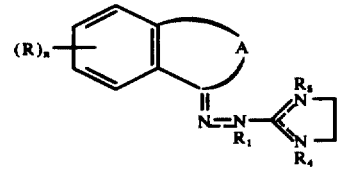

or a pharmaceutically acceptable acid addition salt thereof, in which the dotted lines, R, n, A, $R_1$, $R_4$ and $R_5$ have the meanings indicated in claim 1.

3. A compound according to claim 2, in which "A" stands for a methylene group optionally substituted with alkyl having 1 to 4 carbon atoms.

4. A compound according to claim 2, in which "A" stands for an ethylene group optionally substituted with alkyl having 1 to 4 carbon atoms.

5. A compound according to claim 3, in which R is present at one or both positions 4 and 6.

6. A compound according to claim 4, in which R is present at one or both positions 4 and 6.

* * * * *